United States Patent
Eijgendaal et al.

(10) Patent No.: US 7,405,216 B2
(45) Date of Patent: *Jul. 29, 2008

(54) STABLE CRYSTALLINE FORM OF BIFEPRUNOX MESYLATE (7-[4-([1,1'-BIPHENYL]-3-YLMETHYL)-1-PIPERAZINYL]-2(3H)-BENZOXAZOLONE MONOMETHANESULFONATE)

(75) Inventors: Irene Eijgendaal, Weesp (NL); Gerrit Klein, Weesp (NL); Maria J. L. Terhorst-Van Amstel, Weesp (NL); Klaas Zwier, Weesp (NL); Nico Bruins, Weesp (NL); Hendrikus T. Rigter, Weesp (NL); Erik Gout, Weesp (NL)

(73) Assignee: Solvay Pharmaceuticals, B.V. (NL)

( * ) Notice: Subject to any disclaimer, the term of this patent is extended or adjusted under 35 U.S.C. 154(b) by 703 days.

This patent is subject to a terminal disclaimer.

(21) Appl. No.: 10/920,361

(22) Filed: Aug. 18, 2004

(65) Prior Publication Data

US 2006/0040932 A1 Feb. 23, 2006

(51) Int. Cl.
*A61K 31/501* (2006.01)
*C07D 413/06* (2006.01)

(52) U.S. Cl. .................. 514/254.02; 544/368
(58) Field of Classification Search ............ 514/254.02; 544/368
See application file for complete search history.

(56) References Cited

U.S. PATENT DOCUMENTS

2004/0077631 A1    4/2004    Van Aar et al.

FOREIGN PATENT DOCUMENTS

| EP | 0 908 458 A1 | 4/1999 |
|---|---|---|
| EP | 0 189 612 A1 | 8/2006 |
| WO | WO 97/36893 | 10/1997 |
| WO | WO 00/29397 | 5/2000 |
| WO | WO 01/74365 | 10/2001 |
| WO | WO 02/066449 | 8/2002 |
| WO | WO 2006/032202 | 3/2006 |
| WO | WO 2006/087369 | 8/2006 |
| WO | WO 2007/002341 | 3/2007 |

OTHER PUBLICATIONS

U.S. Appl. No. 11/727,173, filed Feb. 2007, Eijgenaal et al.*
U.S. Appl. No. 10/920,386, Eijgendaal et al.
Halebian et al., "Pharmaceutical Applications of Polymorphism," *Journal of Pharmaceutical Sciences*, 58(8):911-929 (1969).
European Search Report for EP 03 10 2573.
Copending U.S. Appl. No. 11/354,652, filed Feb. 16, 2006.
"Bifeprunox—Atypical Antipsychotic Drug," Drug Development Technology, pp. 1-3, 2007, www.drugdevelopment-technology.com/projects/bifeprunox/.
"Solvay Announces New Drug Plans for Schizophrenia," Schizophernia Daily New Blog, pp. 1-4 (2004), www.schizophrenia.com/sznews/archives/000573.html.
(XP-001061442) Johnston, L.C. et al., "134P: The Novel Dopamine D2 Receptor Partial Agonist, SLV-308, Reverses Motor Disability in MPTO-Lesioned Common Marmosets (Callithrixjacchus)," British Journal of Pharmacology, vol. 133, No. 2 (2001).
(XP-001061489) Feenstra, R. et al., "Antiparkinsonian Antidepressant Anxiolytic Dopamine D2 Partial Agonist 5-HT1A Agonist," Drugs of the Future, vol. 26, No. 2, 2001, pp. 128-132.
(XP-001197381) McCreary, et al., "SLV308: A Novel Antiparkinsonian Agent With Antidepressant and Anxiolytic Efficacy," Abstracts of the Society for Neuroscience (2001).
(XP-002412435) Hesselink, M. et al., "308, A Molecule Combining Potent Partial Dopamine b2 Receptor Agonism with Serotonin 5-HT1A Receptor Agonism: In vitro and in vivo neuro-chemistry," 31st Annual Meeting of the Society for Neuroscience (2001).
(XP-002412436) Johnston, L.C. et al., "SLV308: Antiparkinsonian Effects in the MPTP-Treated Common Marmoset (*Callithrix jacchus*)," 31st Annual Meeting of the Society for Neuroscience (2001).
(XP-002412438) Long Act Sustained-Release Formulations for Treating Parkinson's Disease, Comprise a Dopamine Receptor Agonist and Biodegradable Pharmaceutical Polymer Excipient for Injection Transplant, Corresponds to WO 2006/032202.
(XP008033520) Wolf, William A., "SLV-308 Solvay," Current Opinion in Investigational Drugs, vol. 4, No. 7, 2003, pp. 878-882.
Allen, et al. "A Review of Clinical and Pathophysiologic Features," Journal of Clinical Neurophysiology, vol. 18, No. 2, 2001, pp. 128-147.

(Continued)

*Primary Examiner*—James O. Wilson
*Assistant Examiner*—Ebenezer Sackey
(74) *Attorney, Agent, or Firm*—Finnegan, Henderson, Farabow, Garrett & Dunner, L.L.P.

(57) ABSTRACT

The invention relates to a stable polymorphic form of the compound 7-[4-([1,1'-biphenyl]-3-ylmethyl)-1-piperazinyl]-2(3H)-benzoxazolone monomethanesulfonate (INNM bifeprunox mesylate), a method for the preparation of said polymorphic form and its use in pharmaceutical products, especially in pharmaceutical products for the treatment of psychotic disorders and Parkinson's disease.

25 Claims, 9 Drawing Sheets

OTHER PUBLICATIONS

Allen, et al., "Augmentation of the Restless Legs Syndrome With Carbidopa/Levedopa," Sleep, vol. 19, No. 3, 1996, pp. 205-213.

Bara-Jiminez et al., "Effects of Serotonin 5-HT1A Agonist in Advanced Parkinson's Disease," Movement Disorders, vol. 20, No. 8, 2005, pp. 932-936.

Bennett, et al., "Pramipexole—A new dopamine agonist for the treatment of Parkinson's Disease," Journal of Neurological Sciences, vol. 163, 1999, pp. 25-31.

Berendsen, et al., "Selective Activation of 5HT1A Receptors Induces Lower Lip Retraction in the Rat," Pharmacology Biochemistry & Behavior, vol. 33, pp. 821-827, 1989.

Bibbiani, et al., "Serotonin 5-HT1A Agonist Improves Motor Complications In Rodent and Primate Parkinsonian Models," Neurology, vol. 57, 2001, pp. 1829-1834.

Bickel, M.H., "The Pharmacology and Biochemistry of N-Oxides," Pharmacological Reviews, vol. 21, No. 4, pp. 325-355, 1969.

Blandini, et al., "Functional Changes of the Basal Ganglia Circuitry in Parkinson's Disease," Progress in Neurobiology, vol. 62, 2000, pp. 63-88.

Chesson, et al., "Practice Parameters for the Treatment of Restless Legs Syndrome and Periodic Limb Movement Disorder," Sleep, vol. 22, No. 7, 1999, pp. 961-968.

Christoffersen, et al., "Reversal of Haloperiodol-Induced Extrapyramidal Side Effects in Cebus Monkeys by 8-Hydroxy-2-(di-n-propylamino)tetralin and Enantiomers," Neuropsychopharmacology, vol. 18, No. 5, 1998, pp. 399-402.

Costall et al., "Differential actions of typical and atypical neuroleptic agents on two behavioural effects of apomorphine in the mouse," Proceedings of the B.P.S., pp. 381-381, 1978.

Creese et al., "3H-Spiroperidol Labels Dopamine Receptors in Pituitary and Brain," European Journal of Pharmacology, 46, pp. 377-381, 1977.

Earley, et al., "Movements During Sleep: Pergolide and Carbidopa/Levedopa Treatment of the Restless Legs Syndrome and Periodic Leg Movements in Sleep in a Consecutive Series of Patients," Sleep, vol. 19, No. 10, 1996, pp. 801-810.

Feenstra, et al., "New 1-Aryl-4-(biarylmethylene) piperazines as Potential Atypical Antipsychotics Sharing Dopamine Dz-Receptor and Serotonin 5-HT1A-Receptor Affinities," Bioorganic & Medicinal Chemistry Letters, vol. 11, 2001, pp. 2345-2349.

Feenstra, et al., "New Approaches for Psychosis Treatment: Design, Synthesis and SAR of Ligands Binding to Dopamine-D2- and Serotonin 5-HT1A Receptors," Drugs of the Future, vol. 27, Suppl. A, p. 226 (P237), XVIIth International Symposium on Medicinal Chemistry (2002).

Fleischhacker, "Clozapine: A Comparison With Other Novel Antipsychotics," J. Clin Psychiatry, vol. 60, No. 12, 1999, pp. 30-34.

Gozlan, et al., "Identification of presynaptic serotonin autoreceptors using a new ligand: 3H-PAT," Nature, vol. 305, pp. 140-142, 1983.

Hening, et al., "Dyskinesias While Awake and Periodice Movements In Sleep In Restless Legs Syndrome: Treatment with Opioids," Neurology, vol. 36, 1986, pp. 1363-1366.

Hening, et al., "The Treatment of Restless Legs Syndrome and Periodic Limb Movement Disorder," Sleep, vol. 22, No. 7, 1999, pp. 970-999.

Hesselink, M.B., et al., "P2151""DU127090, SLV308 and SLV318: Characterization of a Chemically Related Class of Partial Dopamine Agonists with Varying Degrees of 5-HT1A Agonism," EFNS European Journal of Neurology, vol. 10 (Suppl. 1), 2003, pp. 125-204.

Hornykiewicz, Oleh, "Dopamine (3-Hydroxytyramine) and Brain Function," Pharmaceutical Reviews, vol. 18, No. 2, 1966, pp. 925-964.

Jankovic, "Natural Course and Limitations of Levodopa Therapy," Neurology, vol. 43, No. 2, Supplement 1, 1993, pp. S1-14 thru S1-17.

Jenner, Peter, "Pharmacology of Dopamine Agonists in the Treatment of Parkinson's Disease," Neurology vol. 58 (Suppl. 1), 2002, pp. S1-S8.

Johnston, et al., P2158, "Association between Instrinsic Activity and the Antiparkinsonian Effects of a Novel Dopamine D2 Agonist series in the 1-methyl-4phenyl-1,2,3,6-tetrahydeopyridine Treated Primate Model of Parkinson's Disease," EFNS European Journal of Neurology, vol. 10 (Suppl. 1), 2003, pp. 169-170.

Jost, et al., "Efficacy and tolerability of Stalevo® in Patients with Parkinson's Disease Experiencing Wearing-off," Akt Neurol, vol. 32, Supplement 6, 2005, pp. S318-S325 (XP009074453).

Kannari, et al., "Tandospirone Citrate, selective 5-HT1A Agonist, Alleviates L-DOPA-Induced Dyskinesia in Patients with Parkinson's Disease," Brain and Nerve, vol. 54, No. 2, 2002, pp. 133-137.

Kim, et al., "Risperidone Dosing Pattern and Clinical Outcome in Psychosis: An Analysis of 1713 Cases," J. Clin Psychiatry, vol. 66, No. 7, 2005, pp. 887-893.

Lange, et al., "Terguride Stimulates Locomotor Activity at 2 Months but Not 10 Months after 1-methyl-4-phenyl-1,2,3,6-tetrahydropyridine Treatment of Common marmosets," European Journal of Pharmacology, vol. 212, 1992, pp. 247-252.

Langston, et al., "MPTP: Current Concepts and Controversies," Clinical Neuropharmacology, vol. 9, No. 6, 1986, pp. 485-507.

Langston, et al., "MPTP-induced Parkinsonism in Human and Non-human Primates—Clinical and Experimental Aspects," Acta Neurol Scan, vol. 70 (Suppl. 100), 1984 pp. 49-54.

Lledó, A., "Dopamine Agonists: The Treatment for Parkinson's Disease in the XXI Century?," Parkinsonism and Related Disorders, vol. 7, 2001, pp. 51-58.

Lozano, et al., "New Developments in Understanding the Etiology of Parkinson's Disease and in its Treatment," Current Opinion in Neurobiology, vol. 8, 1998, pp. 783-790.

Lundbeck, et al., "Bifeprunox Mesilate," Drugs of the Future, vol. 29, No. 9, 2004, pp. 938-939.

McCreary, et al., "SLV308: A Novel Antiparkinsonian Agent With Antidepressant and Anxiolytic Efficacy," 31st Annual Meeting of the Society for Neuroscience Abstracts, vol. 27, Part 1, 2001, p. 531.

McCreary, et al., "The in vitro characterization of SLV308: A Novel Dopamine Ds/D3 partial Agonist and 5-HT1A Full Agonist for the Treatment of Parkinson's Disease," Movement Disorders, vol. 21, Suppl. 13, pp. S79-S80, 2006.

Olanow, et al., "Multicenter, Open-Label, Trial of Sarizotan in Parkinson Disease Patients With Levodopa-Induced Dyskinesias (the Splendid Study)," Clin Neuropharmacol, vol. 27, No. 2, 2004, pp. 58-62.

Pearce, et al., "De Novo Administration of Ropinirole and Bromocriptine Induces Less Dyskinesia Than L-Dope in the MPTP-Treated Marmoset," Movement Disorders, vol. 13, No. 2, 1998, pp. 234-241.

Pollmächer, et al., "Periodic Leg Movements (PLM): Their Relationship to Sleep Stages," Sleep, vol. 16, No. 6, 1993, pp. 572-577.

Rascol, et al., "A Five-Year Study of The Incidence of Dyskinesia In Patients With Early Parkinson's disease Who Were Treated With Ropinirole or Levodopa," The New England Journal of Medicine, vol. 342, No. 20, 2000, pp. 1484-1491.

Robichaud et al., Annual Reports in Medicinal Chemistry, Recent Advances in Selective Serotonin Receptor Modulation, pp. 11-20 (2000).

Salomon, et al., "A Highly Sensitive Adenylate Cyclase Assay," Analytical Biochemistry, 58, pp. 541-548, 1974.

Sorbera, et al., "Treatment of Bipolar Disorder Treatment of Schizophrenia Dopamine D2 Receptor Partial Agonist 5-HT1A Receptor Agonist," Drugs of the Future, pp. 992-997, 2005, vol. 30, No. 10.

Taniguchi et al., "Clozapine Dosage and Titration," Annals of Pharmacotherapy, vol. 30, No. 7-8, 1996, p. 883.

Tenbrink et al., Annual Reports in Medicinal Chemistry, Recent Advances in Dopamine D3 and D4 Receptor Ligands and Pharmacology, pp. 43-51 (1994).

Vliet, B.J. Van, et al., "DU 127090: A Highly Potent, Atypical Dopamine Receptor Ligand—High Potency But Low Efficacy at Dopamine D2 Receptors In Vitro," P.2 Psychotic Disorders Andantipsychotics, European College of Neuropsychopharmacology, vol. 10, No. 3, 2000, p. S294.

Weiss et al., "Corticotropin-Peptide Regulation of Intracellular Cyclic AMP Production in Cortical Neurons in Primary Culture," Journal of Nurochemistry, vol. 45, No. 3, pp. 869-874, 1985.

Widmark, "Studies in the concentration of indifferent narcotics in blood and tissues," Acta Medica Scandinavica, 52, pp. 87-164, 1919.

Copending U.S. Appl. No. 10/920,386, filed Aug. 18, 2004.

Copending U.S. Appl. No. 11/727,173, filed Mar. 23, 2007.
Copending U.S. Appl. No. 11/743,049, filed May 1, 2007.
Copending U.S. Appl. No. 11/762,206, filed Jun. 13, 2007.
Copending U.S. Appl. No. 11/762,239, filed Jun. 13, 2007.
Copending U.S. Appl. No. 11/847,197, filed Aug. 29, 2007.
Copending U.S. Appl. No. 11/847,458, filed Aug. 30, 2007.

* cited by examiner

Figure 1: XRPD pattern of polymorphic form α of bifeprunox mesilate
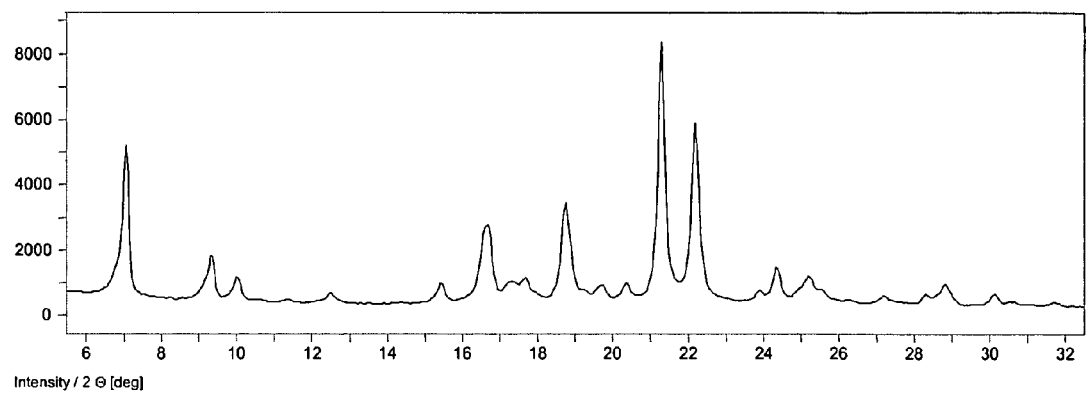
Figure 2: DSC trace of polymorphic form α of bifeprunox mesilate
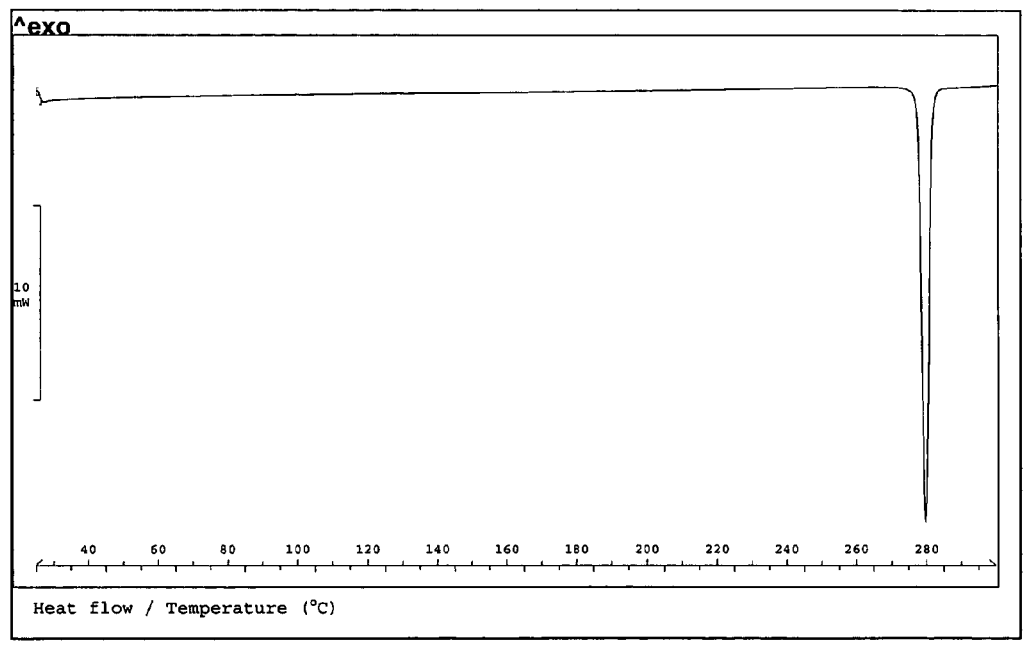

Figure 3: IR (ATR) spectrum of polymorphic form α of bifeprunox mesilate
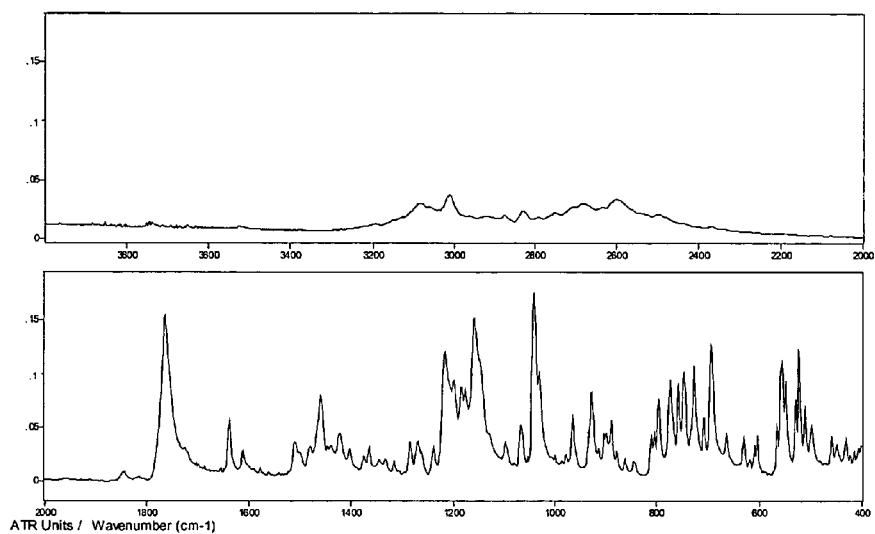
Figure 4: 13C solid state NMR spectrum of polymorphic form α of bifeprunox mesilate
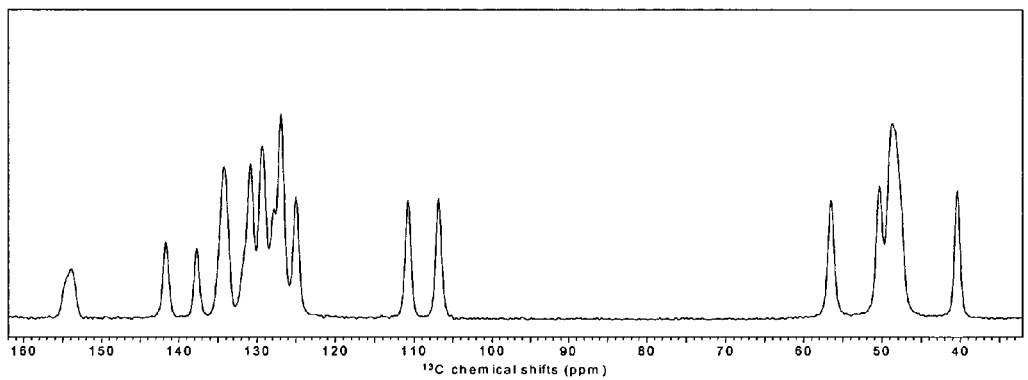

Figure 5: Configuration of polymorphic form *a* of bifeprunox mesilate derived from X-ray crystallography
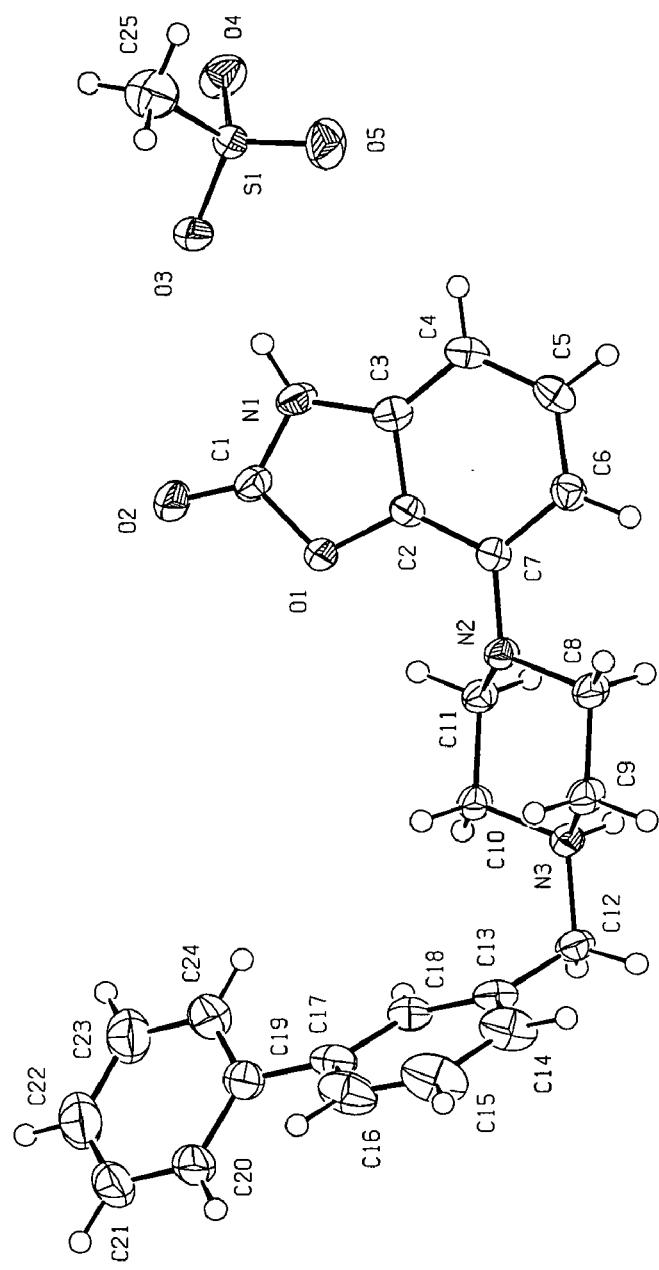

Figure 6: XRPD pattern of polymorphic form γ of bifeprunox mesilate
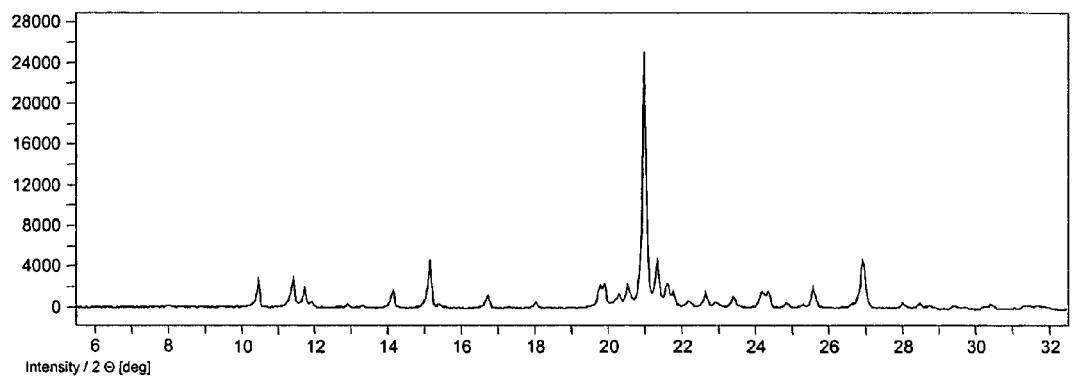
Figure 7: DSC trace of polymorphic form γ of bifeprunox mesilate
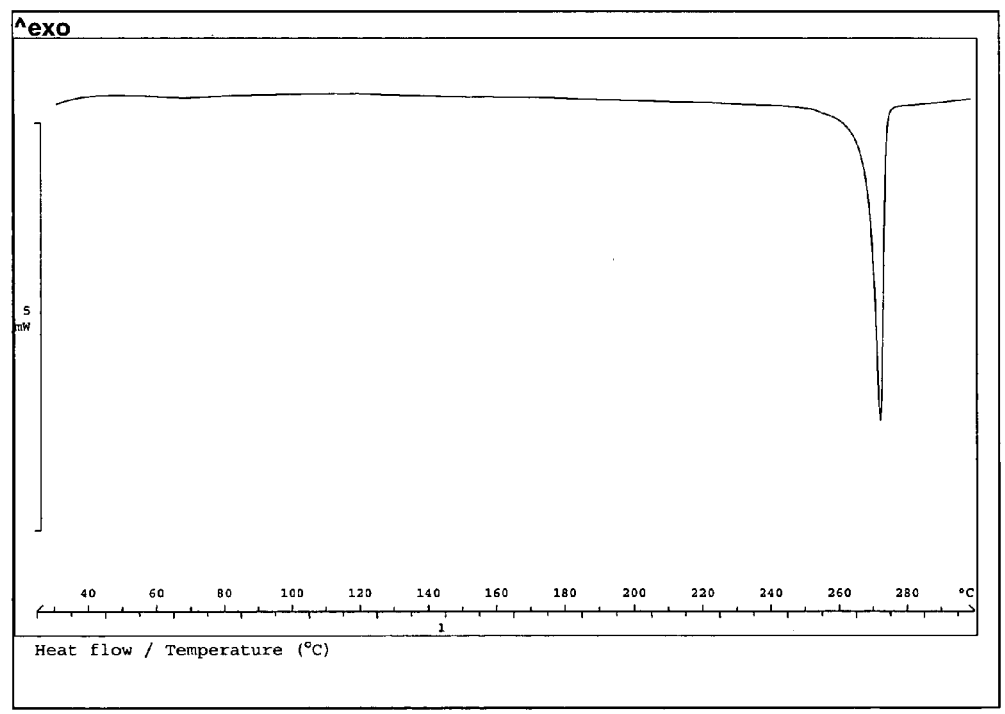

Figure 8: IR (ATR) spectrum of polymorphic form γ of bifeprunox mesilate
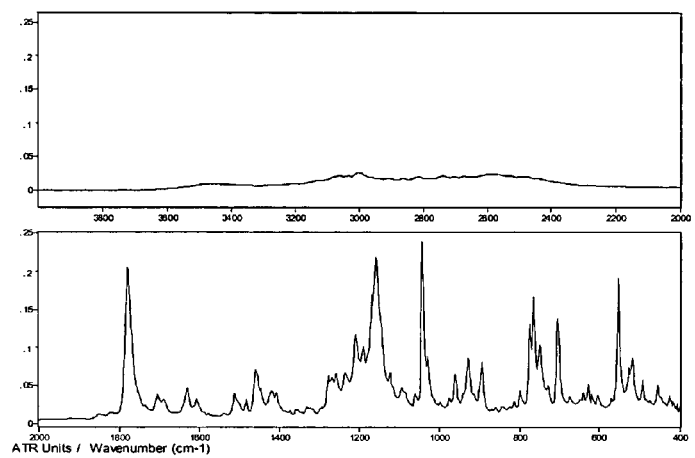
Figure 9: 13C solid state NMR spectrum of polymorphic form γ of bifeprunox mesilate
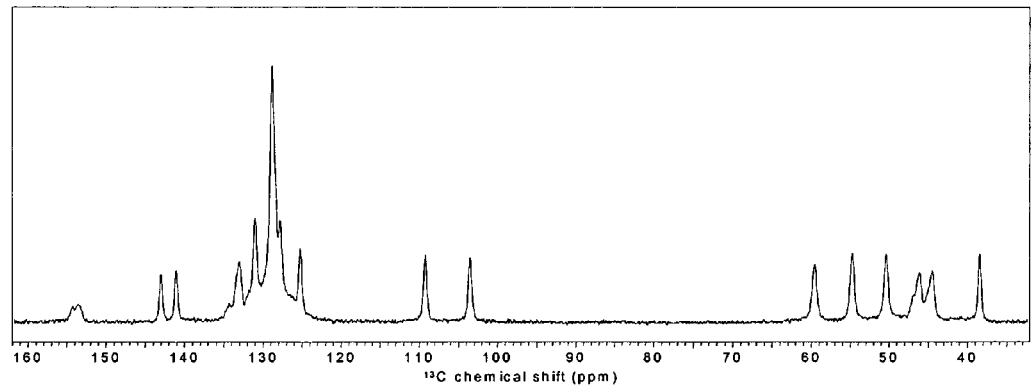

Figure 10: Configuration of polymorphic form γ of bifeprunox mesilate derived from X-ray crystallography
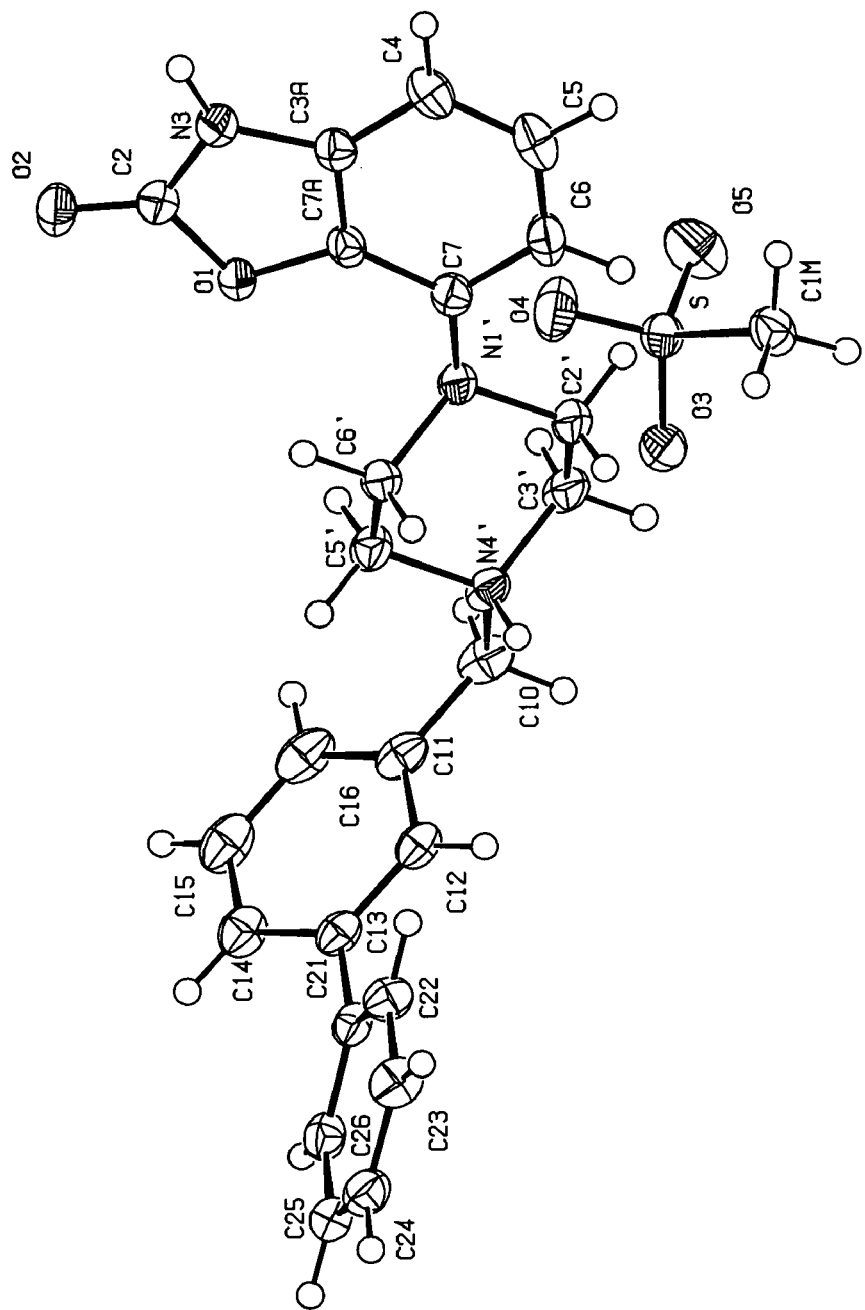

Figure 11: XRPD pattern of polymorphic form δ of bifeprunox mesilate
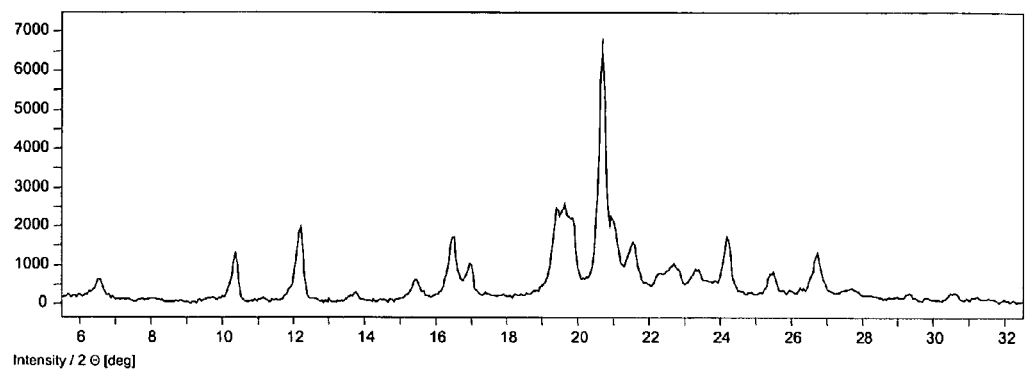
Figure 12: DSC trace of polymorphic form δ of bifeprunox mesilate
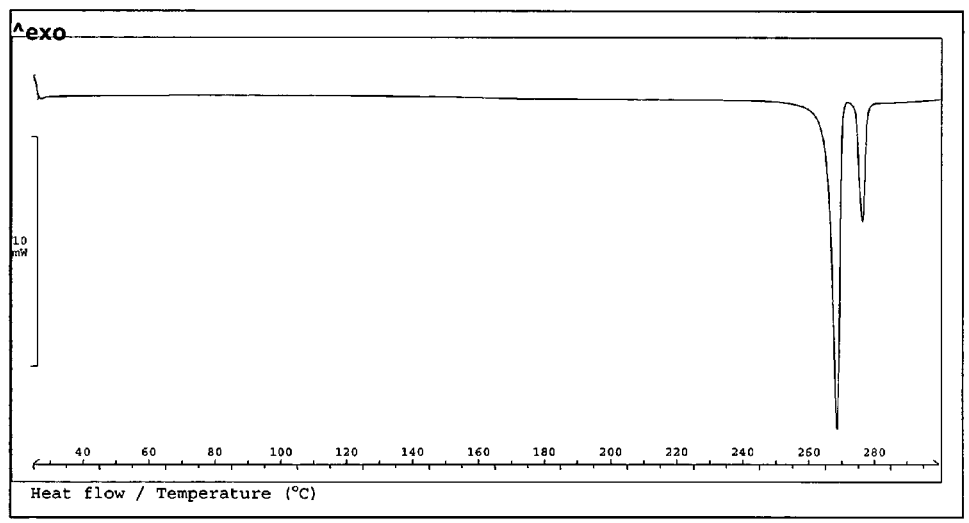

Figure 13: IR (ATR) spectrum of polymorphic form δ of bifeprunox mesilate
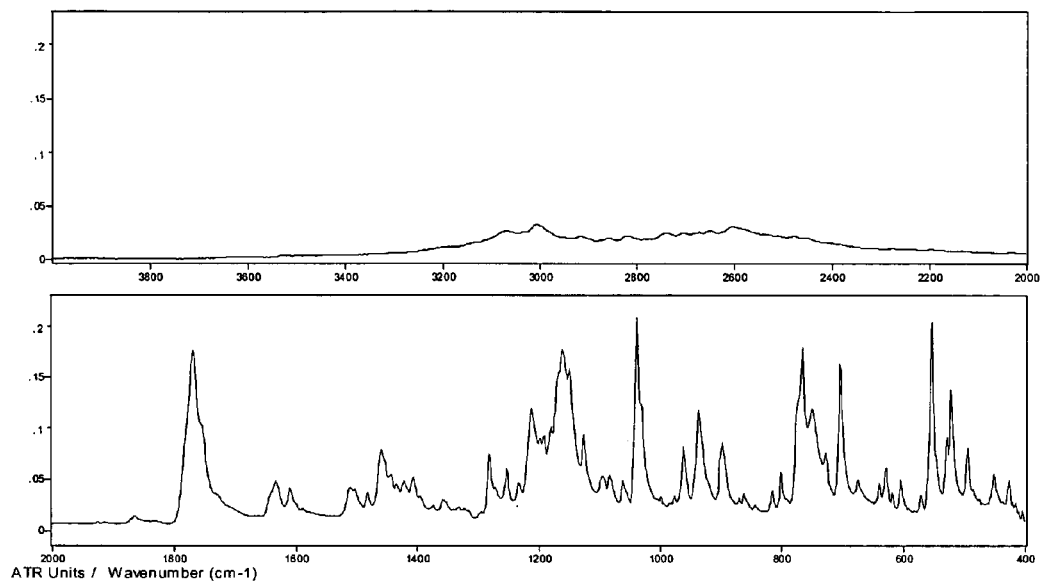
Figure 14: 13C solid state NMR spectrum of polymorphic form δ of bifeprunox mesilate
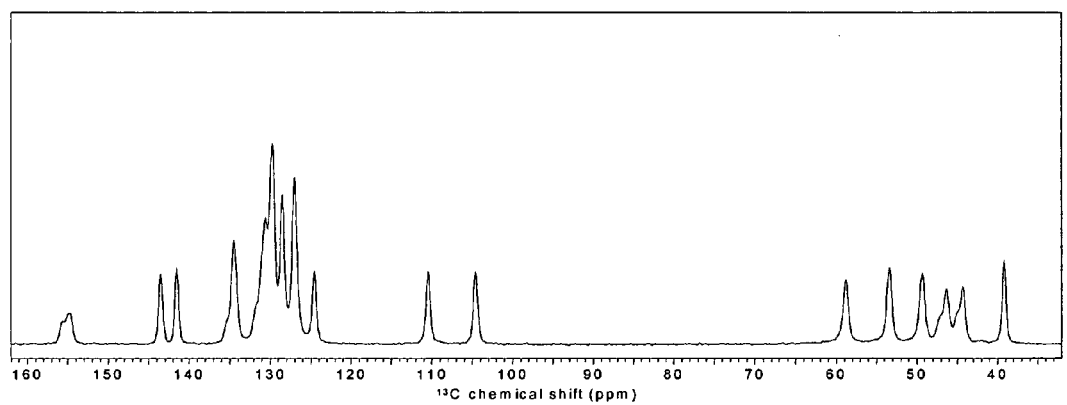

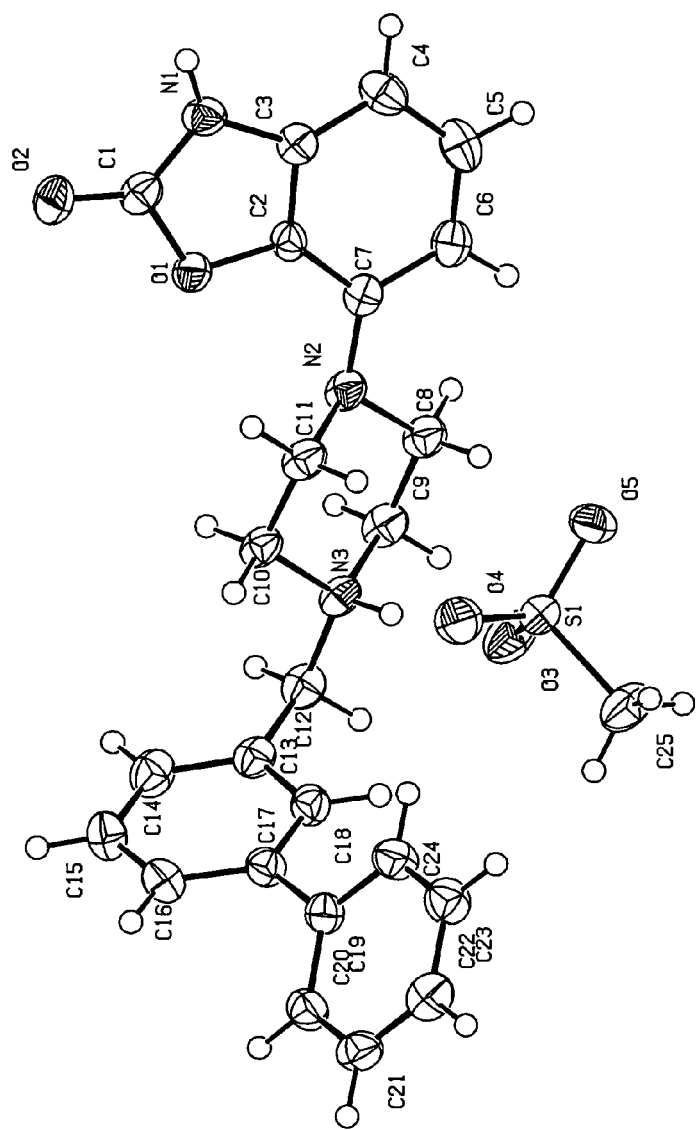
Figure 15: Configuration of polymorphic form δ of bifeprunox mesilate derived from X-ray crystallography

STABLE CRYSTALLINE FORM OF BIFEPRUNOX MESYLATE (7-[4-([1,1'-BIPHENYL]-3-YLMETHYL)-1-PIPERAZINYL]-2(3H)-BENZOXAZOLONE MONOMETHANESULFONATE)

The present invention relates to a stable polymorphic form of the compound 7-[4-([1,1'-biphenyl]-3-ylmethyl)-1-piperazinyl]-2(3H)-benzoxazolone monomethane-sulfonate a method for the preparation of said polymorphic form and its use in pharmaceutical products, especially in pharmaceutical products for the treatment of psychotic disorders and Parkinson's disease.

The mesylate of the compound 7-[4-([1,1'-biphenyl]-3-ylmethyl)-1-piperazinyl]-2(3H)-benzoxazolone monomethanesulfonate (INNM bifeprunox mesilate) has the formula

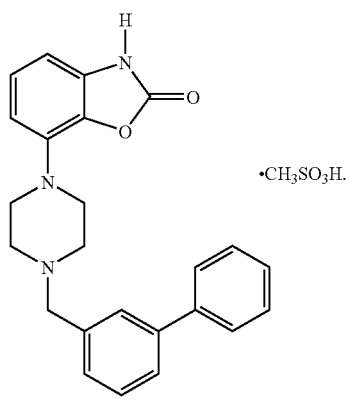

(I)

The hydrochloric acid salt of this compound (7-[4-([1,1'-biphenyl]-3-ylmethyl)-1-piperazinyl]-2(3H)-benzoxazolone (bifeprunox) is described and claimed in WO97/36893 and the monomethanesulfonate salt is described and claimed in WO02/066449. In the second patent publication the direct formation of the monomethanesulfonate salt by the reaction between the reactive mesylate ester of N,N,N-bis(2-ethanol)-m-phenylbenzyl amine and 7-amino-2(3H)-benzoxazolone is disclosed.

The inventors have now found that by the method described in WO02/066449 bifeprunox mesylate is normally obtained as a crude product (melting range indicated in WO02/066449 as 263-275° C.) in a polymorphic form further indicated in this application as polymorph δ (delta). Upon further purification the product is obtained in two different crystal modifications or a mixture of these two modifications. The first of said two modifications is the already mentioned polymorph δ (delta) and has a melting point in pure form of 265° C. The second modification is further indicated as polymorph γ (gamma). When the γ polymorph is predominantly is obtained, it is in almost all cases obtained in a mixture of said polymorph with polymorph δ, the mixture having a melting point of about 273° C.

During further investigations it has appeared that polymorphs γ and δ are metastable, and therefore may have serious drawbacks when used in a pharmaceutical formulation. The unpredictable formation of one of the two polymorphs γ and δ or a mixture thereof is also undesirable. It is therefore the object of the present invention to provide a stable crystalline form of 7-[4-([1,1'-biphenyl]-3-ylmethyl)-1-piperazinyl]-2(3H)-benzoxazolone monomethanesulfonate for pharmaceutical use which can be produced in a reproducible manner.

It has now surprisingly been found that 7-[4-([1,1'-biphenyl]-3-ylmethyl)-1-piperazinyl]-2(3H)-benzoxazolone monomethanesulfonate also has another crystalline polymorphic form (referred to below as polymorph α (alpha)) which does not have the disadvantages of the earlier mentioned polymorphs. This crystalline form of bifeprunox mesylate is more thermodynamically stable. Polymorphic form α does not undergo conversion, even at high atmospheric humidity or higher temperature. Furthermore this crystalline form crystallizes in the form of large crystals which can be easily be filtrated and having a high purity. Therefore this polymorph α is particularly suitable for the formulation of bifeprunox mesylate in a solid form, if desired after particle size reduction.

BRIEF DESCRIPTION OF THE DRAWINGS

FIG. 1 shows an XRPD pattern of polymorphic form α of bifeprunox mesylate.

FIG. 2 shows a DSC trace of polymorphic form α of bifeprunox mesylate.

FIG. 3 shows an IR (ATR) spectrum of polymorphic form α of bifeprunox mesylate.

FIG. 4 shows a $^{13}$C solid state NMR spectrum of polymorphic form α of bifeprunox mesylate.

FIG. 5 shows a configuration of polymorphic form α of bifeprunox mesylate derived from X-ray crystallography.

FIG. 6 shows an XRPD pattern of polymorphic form γ of bifeprunox mesylate.

FIG. 7 shows a DSC trace of polymorphic form γ of bifeprunox mesylate.

FIG. 8 shows an IR (ATR) spectrum of polymorphic form γ of bifeprunox mesylate.

FIG. 9 shows a $^{13}$C solid state NMR spectrum of polymorphic form γ of bifeprunox mesylate.

FIG. 10 shows a configuration of polymorphic form γ of bifeprunox mesylate derived from X-ray crystallography.

FIG. 11 shows an XRPD pattern of polymorphic form δ of bifeprunox mesylate.

FIG. 12 shows a DSC trace of polymorphic form δ of bifeprunox mesylate.

FIG. 13 shows an IR (ATR) spectrum of polymorphic form δ of bifeprunox mesylate.

FIG. 14 shows a $^{13}$C solid state NMR spectrum of polymorphic form δ of bifeprunox mesylate.

FIG. 15 shows a configuration of polymorphic form δ of bifeprunox mesylate derived from X-ray crystallography.

The crystalline polymorphic form of bifeprunox mesylate according to the present invention is defined by the following physicochemical parameters X-Ray diffraction patterns (Table 1 and FIG. 1);

The melting point of polymorphic form α is 277° C. (DSC heating rate 10 K/min) (see DSC thermogram, FIG. 2);

IR spectrum (Table 2 and FIG. 3); The most important IR absorption bands of form α of bifeprunox mesylate which can be used to distinguish this form from forms γ and δ are given in Table 2a;

Solid state $^{13}$C-NMR spectrum (Table 3 and FIG. 4); The most important $^{13}$C-NMR shifts of form α of bifeprunox mesylate which can be used to distinguish this form from forms γ and δ are given in Table 3a;

Single crystal X-ray diffraction (Tables 4 and 5 and FIG. 5).

All data herein are understood to be approximate and subject to normal measurement error depending e.g. on the apparatus used and other parameters influencing peak positions and peak intensities.

TABLE 1 shows characteristic X-ray powser diffractions of forms α, γ and δ of bifeprunox mesylate. FIG. 1 provides a representative XRPD pattern of polymorphic form α of bifeprunox mesylate.

| Form | Characteristic reflexes (expressed in degree of diffraction angle 2θ at room temperature) |
|---|---|
| α | 7.0, 9.3, 10.0, 12.5, 15.4, 16.7, 17.2, 17.4, 17.7, 18.7, 21.3, 22.2, 25.2, 27.2, 28.3, 28.8, 30.1 |
| γ | 10.4, 11.4, 11.7, 14.1, 15.1, 21.0, 26.9 |
| δ | 6.4, 10.2, 12.1, 16.4, 16.8, 19.3, 19.7, 20.6, 24.1, 26.6 |

TABLE 2 show characteristic IR absorption bands of forms α, γ and δ of bifeprunox mesylate. FIG. 2 provides a representative IR spectrum of polymorphic form α of bifeprunox mesylate.

| Form | Characteristic IR absorption bands (expressed in cm$^{-1}$) |
|---|---|
| α | 1764, 1636, 1284, 1217, 809, 795, 746, 694, 663, 509 |
| γ | 1777, 1279, 1258, 1210, 1124, 800, 764, 749, 627, 518 |
| δ | 1865, 1769, 1434, 1282, 1253, 1212, 1126, 935, 767, 751 |

TABLE 2a shows important IR absorption bands of forms α, γ and δ of bifeprunox mesylate which can be used to distinguish the three forms.

| Form | Characteristic IR absorption bands (expressed in cm$^{-1}$) |
|---|---|
| α | 1764, 1217, 795, 746, 694 |
| γ | 1777, 1210, 764, 749, 518 |
| δ | 1769, 1212, 935, 767, 751 |

TABLE 3 shows characteristic $^{13}$C solid state NMR chemical shifts in forms α, γ and δ of bifeprunox mesylate. FIG. 3 provides a representative $^{13}$C solid state NMR spectrum of polymorphic form α of bifeprunox mesylate.

| Form | Characteristic chemical shift (expressed in ppm relative to glycine (δ$_c$ = 176.03 for the C=O resonance) |
|---|---|
| α | 40.4, 48.7, 50.3, 56.5, 106.8, 110.7, 124.9, 126.9, 127.8, 129.2, 130.8, 134.2, 137.7, 141.6, and *153.8. |
| γ | 38.2, *44.3, *45.9, 50.1, 54.5, 59.4, 103.5, 109.3, 125.3, 127.9, 128.9, 131.1, 133.2, 134.5, 141.2, 143.2 and *153.7 |
| δ | 39.1, *44.3, *46.3, 49.3, 53.4, 58.8, 104.6, 110.4, 124.6, 127.0, 128.5, 129.7, 130.5, 134.4, 141.5, 143.5, and *154.7 |

*denotes carbon resonances which show typical asymmetric residual quadrupolar splittings. Chemical shift are given for the high-field resonance maximum TABLE 3a shows important $^{13}$C solid state NMR chemical shift bands of forms α, γ and δ of bifeprunox mesylate which can be used to distinguish the three forms.

| Form | Characteristic chemical shift (expressed in ppm relative to glycine (δ$_c$ = 176.03 for the C=O resonance) |
|---|---|
| α | 40.4, 48.7, 56.5, 106.8 and 137.7 |
| γ | 38.2, 54.5, 103.5, 109.3 and 133.2 |
| δ | 39.1, 49.3, 53.4, 58.8 and 104.6 |

TABLE 4 shows relevant single crystal X-ray diffraction data collection parameters for the crystal structure determination of forms α, γ and δ of bifeprunox mesylate.

| | Alpha (α) | Gamma (γ) | Delta (δ) |
|---|---|---|---|
| Temperature (K) | 150 | 133 | 150 |
| Wavelength (Å) | 0.71073[1] | 0.71073 | 0.71073 |
| Crystal size (mm × mm × mm) | 0.10 × 0.15 × 0.27 | 0.24 × .13 × 0.07 | 0.10 × 0.15 × 0.35 |
| Crystal system | triclinic | monoclinic | triclinic |
| Space group | P-1 | P2$_1$/c | P-1 |
| Z | 2 | 4 | 2 |
| Unit cell dimensions; a (Å) | 9.823 | 9.0975 | 9.1832 |
| B (Å) | 10.737 | 15.269 | 9.3963 |
| C (Å) | 12.690 | 17.128 | 14.106 |
| α (°) | 98.553 | 90 | 76.968 |
| β (°) | 93.749 | 100.694 | 83.809 |
| Γ (°) | 116.097 | 90 | 89.157 |
| Calculated density (g cm$^{-3}$) | 1.481 | 1.368 | 1.3556 |
| Completeness of data (%) | 100.0 | 100.0 | 99.8 |
| Total number of reflections | 27105 | 23759 | 27207 |
| Number of unique reflections | 5355 | 5809 | 4149 |
| Nr. Of refined parameters | 314 | 316 | 314 |

[1] (Mo Kα radiation)

TABLE 5 shows atomic coordinates (×10⁴) and equivalent isotropic displacement parameters ($Å^2 \times 10^3$) for the crystal structure of form α of bifeprunox mesylate. U(eq) is defined as one third of the trace of the orthogonalized $U_{ij}$ tensor.

| | x | y | z | U(eq) |
|---|---|---|---|---|
| O1 | 3471.7(11) | 3848.0(10) | 2910.8(8) | 26.4(3) |
| O2 | 2785.8(13) | 1499.8(11) | 2541.1(10) | 38.1(4) |
| N1 | 5215.5(15) | 3175.4(14) | 3398.0(11) | 29.3(4) |
| N2 | 3880.6(13) | 6773.4(13) | 3211.0(10) | 24.6(4) |
| N3 | 1702.0(14) | 7879.1(13) | 3177.7(11) | 24.9(4) |
| C1 | 3755.9(18) | 2687.4(17) | 2914.9(13) | 28.6(5) |
| C2 | 4801.7(16) | 5042.8(16) | 3421.0(12) | 23.7(4) |
| C3 | 5896.6(17) | 4637.6(16) | 3727.8(12) | 25.8(5) |
| C4 | 7334.0(17) | 5622.3(17) | 4265.8(12) | 28.3(5) |
| C5 | 7587.8(18) | 7016.7(18) | 4470.3(12) | 30.7(5) |
| C6 | 6489.3(17) | 7425.7(17) | 4145.1(12) | 28.2(5) |
| C7 | 5035.3(17) | 6432.4(16) | 3594.8(12) | 24.3(4) |
| C8 | 4371.2(18) | 8285.6(16) | 3280.4(14) | 29.8(5) |
| C9 | 3141.4(17) | 8515.3(17) | 2694.6(13) | 29.2(5) |
| C10 | 1196.3(17) | 6328.4(15) | 3094.7(13) | 25.8(5) |
| C11 | 2450.2(16) | 6106.0(16) | 3661.4(12) | 25.9(5) |
| C12 | 465.7(18) | 8238.1(17) | 2763.9(13) | 29.1(5) |
| C13 | −273.5(18) | 7526.6(18) | 1622.4(13) | 30.9(5) |
| C14 | 166(2) | 8245(2) | 780.4(15) | 46.7(7) |
| C15 | −586(2) | 7574(3) | −256.4(16) | 57.6(8) |
| C16 | −1734(2) | 6194(2) | −466.0(15) | 49.2(7) |
| C17 | −2206.8(19) | 5456.1(19) | 362.2(13) | 34.9(6) |
| C18 | −1474.4(18) | 6157.3(18) | 1409.5(13) | 30.8(5) |
| C19 | −3495(2) | 4003.7(19) | 170.3(13) | 37.1(6) |
| C20 | −4751(2) | 3585(2) | −623.3(14) | 43.7(6) |
| C21 | −5976(2) | 2260(2) | −766.8(17) | 54.6(7) |
| C22 | −5989(2) | 1318(2) | −129.3(18) | 58.2(8) |
| C23 | −4750(3) | 1709(2) | 655.0(17) | 54.6(7) |
| C24 | −3520(2) | 3039(2) | 804.2(15) | 45.3(6) |
| S1 | 8220.4(4) | 1865.1(4) | 3801.4(3) | 26.8(1) |
| O3 | 6650.8(13) | 1454.8(12) | 3355.9(10) | 40.2(4) |
| O4 | 8282.1(15) | 1197.6(13) | 4711.2(9) | 42.6(4) |
| O5 | 9171.5(14) | 3369.6(12) | 4040.9(11) | 48.7(4) |
| C25 | 8951(2) | 1114(2) | 2801.2(15) | 51.0(7) |

TABLE 6 shows atomic coordinates (× 10⁴) and equivalent isotropic displacement parameters ($Å^2 \times 10^3$) for the crystal structure of form γ of bifeprunox mesylate. U(eq) is defined as one third of the trace of the orthogonalized $U_{ij}$ tensor.

| | x | y | z | U(eq) |
|---|---|---|---|---|
| O(1) | 6610.7(11) | 756.7(7) | 6306.4(6) | 26.6(2) |
| O(2) | 9117.5(12) | 552.8(8) | 6513.4(8) | 40.3(3) |
| C(2) | 7882.4(17) | 240.9(11) | 6352.9(10) | 29.1(4) |
| N(3) | 7439.1(14) | −598.9(9) | 6206.3(8) | 27.4(3) |
| C(3A) | 5878.6(17) | −646.4(10) | 6063.5(9) | 24.5(3) |
| C(4) | 4896.5(18) | −1346.6(11) | 5948.7(9) | 31.7(4) |
| C(5) | 3392.7(19) | −1133.4(11) | 5866.9(10) | 35.5(4) |
| C(6) | 2894.2(18) | −281.1(11) | 5915.0(9) | 32.3(4) |
| C(7) | 3884.2(17) | 428.8(10) | 6069.0(9) | 26.2(3) |
| C(7A) | 5382.3(16) | 199.5(10) | 6119.9(8) | 23.7(3) |
| N(1') | 3465.6(14) | 1286.2(8) | 6230.9(8) | 28.4(3) |
| C(2') | 1876.4(18) | 1434.5(11) | 6215.9(11) | 35.7(4) |
| C(3') | 1661.2(18) | 2283.3(11) | 6630.3(11) | 36.5(4) |
| N(4') | 2322.4(14) | 3039.8(9) | 6262.9(8) | 28.0(3) |
| C(5') | 3942.4(17) | 2861.2(11) | 6265.4(10) | 30.0(4) |
| C(6') | 4103.6(17) | 2010.2(10) | 5840.3(9) | 27.2(3) |
| C(10) | 2051(2) | 3884.9(10) | 6667.0(10) | 35.6(4) |
| C(11) | 2788.0(18) | 4658.9(11) | 6354.2(9) | 30.7(4) |
| C(12) | 2314.0(17) | 4949.2(10) | 5577.8(9) | 27.8(4) |
| C(13) | 3015.0(17) | 5646.9(10) | 5277.0(9) | 26.8(3) |
| C(14) | 4183.8(18) | 6072.6(11) | 5781.3(10) | 33.7(4) |
| C(15) | 4644(2) | 5795.6(12) | 6554.8(11) | 40.5(4) |
| C(16) | 3964.4(19) | 5086.4(12) | 6836.9(10) | 38.5(4) |
| C(21) | 2576.4(16) | 5917.7(10) | 4432.2(9) | 25.3(3) |
| C(22) | 2266.8(17) | 5286.3(11) | 3836.1(9) | 29.8(4) |
| C(23) | 1921.6(19) | 5532.9(11) | 3043.3(10) | 35.0(4) |
| C(24) | 1900.5(18) | 6409.3(11) | 2833.0(10) | 33.3(4) |
| C(25) | 2200.7(17) | 7041.3(11) | 3419.1(10) | 31.8(4) |
| C(26) | 2519.2(17) | 6797.7(10) | 4209.4(10) | 29.3(4) |
| S | 9163.9(4) | −2786.7(3) | 5975.1(2) | 28.4(1) |
| O(3) | 9584.0(13) | −1870.9(7) | 6067.6(8) | 39.5(3) |
| O(4) | 7714.0(13) | −2961.4(8) | 6156.0(8) | 48.0(4) |
| O(5) | 9327.4(15) | −3123.8(9) | 5197.7(7) | 50.7(4) |
| C(1M) | 10484.0(18) | −3388.0(11) | 6647.3(9) | 33.1(4) |

TABLE 7 shows atomic coordinates (× 10⁴) and equivalent isotropic displacement parameters ($Å^2 \times 10^3$) for the crystal structure of form δ of bifeprunox mesylate. U(eq) is defined as one third of the trace of the orthogonalized $U_{ij}$ tensor.

| | x | y | z | U(eq) |
|---|---|---|---|---|
| O1 | 4353.9(14) | 2151.8(14) | 9.8(9) | 31.7(5) |
| O2 | 2013.8(15) | 1799.9(16) | −260.0(11) | 41.7(6) |
| N1 | 3473.0(19) | 3697(2) | −1220.7(13) | 33.0(6) |
| N2 | 7357.2(17) | 2103.5(19) | 550.2(12) | 32.1(6) |
| N3 | 8449.3(17) | 325.4(19) | 2265.2(12) | 30.5(6) |
| C1 | 3130(2) | 2515(2) | −491.7(15) | 31.6(8) |
| C2 | 5441(2) | 3184(2) | −431.7(14) | 27.6(7) |
| C3 | 4912(2) | 4146(2) | −1202.7(15) | 29.5(7) |
| C4 | 5792(2) | 5233(2) | −1804.5(16) | 38.0(8) |
| C5 | 7222(2) | 5295(2) | −1576.5(17) | 40.4(8) |
| C6 | 7745(2) | 4328(2) | −796.9(16) | 35.7(8) |
| C7 | 6862(2) | 3203(2) | −190.9(15) | 29.9(7) |
| C8 | 8926(2) | 2107(2) | 662.0(15) | 36.3(8) |
| C9 | 9346(2) | 659(2) | 1284.5(15) | 36.0(7) |
| C10 | 6854(2) | 364(2) | 2127.3(15) | 33.3(7) |
| C11 | 6484(2) | 1826(2) | 1508.8(14) | 34.0(7) |
| C12 | 8900(2) | −1091(2) | 2896.8(15) | 35.7(8) |
| C13 | 7978(2) | −1468(2) | 3868.2(15) | 32.6(7) |
| C14 | 6997(2) | −2644(2) | 4086.9(17) | 40.5(8) |
| C15 | 6109(2) | −2941(2) | 4966.4(17) | 42.7(8) |
| C16 | 6171(2) | −2068(2) | 5624.7(16) | 39.1(8) |
| C17 | 7146(2) | −888(2) | 5437.5(15) | 32.1(7) |
| C18 | 8054(2) | −613(2) | 4552.0(15) | 32.2(7) |
| C19 | 7171(2) | 74(2) | 6137.9(15) | 31.4(7) |
| C20 | 7068(2) | −494(2) | 7144.3(15) | 34.8(7) |
| C21 | 7028(2) | 422(3) | 7794.2(16) | 38.2(8) |
| C22 | 7099(2) | 1919(2) | 7448.1(16) | 39.7(8) |
| C23 | 7201(2) | 2497(2) | 6453.5(16) | 41.0(8) |
| C24 | 7234(2) | 1589(2) | 5798.4(16) | 37.9(8) |
| S1 | 8731.8(6) | 3909.1(6) | 3076.9(4) | 33.3(2) |
| O3 | 9471.7(16) | 2602.8(12) | 2887.4(12) | 50.3(6) |
| O4 | 7233.7(16) | 3640.6(18) | 3484.5(11) | 50.4(6) |
| O5 | 8877.7(16) | 5117.0(17) | 2228.8(11) | 47.6(5) |
| C25 | 9712(3) | 4404(3) | 3958.1(17) | 48.8(9) |

The polymorphic form α differs substantially from the forms γ and δ in its physicochemical parameters: DSC melting behavior, X-ray diffraction pattern, IR spectrum and solid state $^{13}$C-NMR spectrum. The physicochemical parameter of the forms γ and δ are given in Tables 1-4, 6 and 7 and FIGS. 6-15.

The present invention also relates to bifeprunox mesylate in which at least about 50 weight percent (wt. %) of the bifeprunox mesylate, preferably at least about 60 wt. % thereof, more preferably at least about 80 wt. % thereof, more advantageously, at least about 90 wt. %, yet more preferably at least about 95 wt % of bifeprunox mesylate is in the polymorphic α form and is substantially devoid of any γ or δ polymorphic forms thereof. With substantially devoid is meant an amount of less than 10%, preferably less than 5% w/w. Still more preferably at least about 99% wt. % of bifeprunox mesylate is in the polymorphic α form.

The preparation of the polymorphic form α according to the invention is carried out by recrystallisation from an organic solvent or a mixture of an organic solvent with water, preferably a mixture of a ($C_1$-$C_6$)alcohol and water or a mixture of acetonitrile and water. More preferred are a mixture of 2-propanol and water or a mixture of acetonitrile and water. The most preferred solvent is a mixture of acetonitrile and water. The polymorphic form γ can be prepared by making the free base of bifeprunox directly followed by the addition of methane sulphonic acid and crystallization from methylethylketone.

The polymorphic form α and γ according to the invention can be formulated into dosage forms in which the crystalline active substance is present in the solid form by methods known in the art. Examples of said dosage forms are (optionally coated) tablets, capsules, granular aerosols, suppositories and suspensions, which can be prepared by mixing the polymorphic form α or γ of the active substance with inert pharmaceutically acceptable excipients and carriers. Most preferably the dosage forms are tablets or capsules.

In a preferred formulation of the polymorphic forms α and γ according to the invention the composition contains, apart from the milled and sieved active substance, lactose monohydrate, microcrystalline cellulose, sodium starch glycolate type A, sodium stearyl fumarate and optionally colloidal anhydrous silica. The amount of lactose is between 20 and 90% w/w of the total weight of the tablet core, preferably between 70 and 90% w/w and most preferred between 75 and 85% w/w. The amount of microcrystalline cellulose is between 5 and 90% w/w of the total weight of the tablet core, preferably between 10 and 15% w/w and most preferred between 11 and 12% w/w. The amount of sodium starch glycolate type A is between 0.1% and 2.5% w/w of the total weight of the tablet core, preferably between 0.3 and 0.7% w/w and most preferred about 0.5% w/w. The amount of sodium stearyl fumarate is between 0.1% and 1.5% of the total weight of the tablet core, preferably between 0.6 and 1.3% w/w and most preferred about 1.0% w/w. Collodial anhydrous silica is optionally added to the formulation in order to improve the flow properties of the powder. When added it is preferably added in an amount of between 0.05% and 0.5% w/w of the total weight of the tablet core, preferably about 0.4% w/w. The amount of coating is between 2.0% and 5.0% w/w of the weight of the tablet core, preferably between 3.0 and 4.0% w/w and most preferred about 3.5%.

In a further aspect the invention relates to a method of producing the formulation described above, wherein the active substance having polymorphic form α or γ according to the invention is milled and subsequently mixed with a suitable mixer (e.g. an orbital screw mixer (Nauta mixer) or a combination of a diffusion mixer (bin blender) with a rotating impeller mill (quadro co-mill)) with lactose monohydrate, microcrystalline cellulose, sodium starch glycolate type A, sodium stearyl fumarate and optionally with colloidal anhydrous silica and pressed into tablets of the desired strength. During tabletting the pressure is between 200 and 400 MPa, preferably between 250 and 350 and most preferred about 300 MPa. The product is coated with a colour and taste coating by spraying of a coating suspension onto the tablet core in a suitable coating equipment (e.g. a perforated pan coater or a fluidized bed coater)

The polymorphic form α and γ according to the invention can be used by administering to a living being. Bifeprunox mesylate is especially useful for the treatment of humans suffering from psychotic disorders or Parkinson's disease.

The following examples are only intended to further illustrate the invention, in more detail, and therefore these examples are not deemed to restrict the scope of the invention in any way.

EXAMPLE 1

Preparation of Bifeprunox Mesylate

Example 1a

Preparation of N-(5-chloro-2-hydroxyphenyl)acetamide 143.6 g (1 mole) of 2-amino4-chlorphenol was suspended in 550 ml of methyl t-butyl ether under mild nitrogen purge. The mixture was heated to reflux until the material was dissolved. In 40 minutes 112.3 g of acetic anhydride was added. After the addition the mixture was cooled to 20-25° C. in one hour. After stirring for an additional hour the mixture was cooled to 0-5° C. under stirring and kept on this temperature for an additional hour. The product was filtered off, washed with 200 ml of methyl t-butyl ether twice and dried at 50° C. and 100 mbar under a gentle nitrogen stream till dry. Yield about 92%.

Example 1b

Preparation of N-(5-chloro-2-hydroxy-3-nitrophenyl)acetamide 224.5 g of sulphuric acid (50% w/w) was dissolved in 300 ml of water and cooled to 25° C. while stirring under a mild nitrogen purge. 185.1 g (1 mole) of N-(5-chloro-2-hydroxyphenyl)acetamide prepared according to Example 1a was added to the diluted sulphuric acid and mixed intensively. 4 ml of nitric acid 65% w/w was added to the foam formed on top of the reaction mixture at low stirring speed. The stirring speed was increased and 75 ml of nitric acid 65% w/w was added in 45 minutes, while maintaining the temperature between 23 and 26° C. The mixture was stirred vigorously for an additional 1 hour at 23-26° C. Then the mixture was cooled to 0-5° C. and vigorously stirred at this temperature for 1 hour. The solid was filtered off quickly, washed three times with 300 ml of cold water, sucked for at least 30 minutes and dried at 50° C. and 100 mbar under a gentle nitrogen stream till dry.

The crude product was suspended in 2000 ml 96% ethanol, heated till reflux and refluxed under stirring for about 15 minutes until a clear solution was obtained. The solution was cooled to 25-30° C. in about 1 hour, while stirring slowly, further cooled to 0-5° C. and stirred at this temperature for an additional hour. The solid was filtered off, washed twice with 250 ml of cold 96% ethanol, and dried at 50° C. and 100 mbar under a gentle nitrogen stream till dry. Yield about 78%.

Example 1c

Preparation of 6-amino-4-chloro-2-nitrophenol 230.6 g (1 mole) of N-(5-chloro-2-hydroxy-3-nitrophenyl) acetamide prepared according to Example 1 b was suspended in a mixture of 950 ml of water and 100 ml of 2-propanol under a mild nitrogen purge. 345 ml of 36% w/w hydrochloric acid was added followed by 25 ml of water. The mixture was heated to reflux in about 30° C., while vigorously stirring and refluxed for 2 hours. The mixture was cooled to 0-5° C. in about one hour and stirred for an additional hour at 0-5° C. The solid was filtered off, washed twice with 250 ml of water, and dried at 50° C. and 100 mbar under a gentle nitrogen stream till dry. Yield about 91%.

Example 1d

Preparation of 5-chloro-7-nitro-2(3H)-benzoxazolone 188.6 g (1 mole) of 6-amino-4-chloro-2-nitrophenol prepared according to Example 1c was suspended in 1000 ml of ethyl acetate under mild nitrogen purge and the optional present water was removed by azeotropic distillation of 250 ml of the solvent. The mixture was cooled to 20-25° C. and 224 g of carbonyldiimidazole was added as a slurry in 650 ml of ethyl acetate. An additional 100 ml of ethyl acetate was added and the mixture was vigorously stirred during two hours, without the application of cooling. 1000 ml of water was added and the mixture was stirred for 15 minutes. 1450-1500 ml of ethyl acetate was distilled off at about 200 mBar and about 50° C. The mixture was cooled to 0-5° C., 225 ml of 36% HCl was added and the mixture ws cooled again to 0-5° C. and stirred at this temperature for 15 minutes. The solid was filtered off, washed with 400 ml of 1N HCl, washed twice with 500 ml of cold water and once with 500 ml of cold water/ethanol (4/1), and dried at 50° C. and 100 mbar under a gentle nitrogen stream till dry. Yield about 99%.

Example 1e

Preparation of 7-amino-2(3H)-benzoxazolone 107.5 g (1 mole) of 5-chloro-7-nitro-2(3H)-benzoxazolone prepared according to Example 1d was suspended in 1000 ml of ethanol. 9.25 g of Pd/C 5% and 50 ml of ethanol were added and the mixture was hydrogenated at 4 bar hydrogen pressure for four to six hours at 60-65° C. while vigorously stirring. When the hydrogenation was complete, the mixture was cooled to 45° C. and filtered over Hyflo®. The Hyflo® was washed twice with 175 ml of methanol. 500 ml of solvent was distilled off under reduced pressure at 50° C., followed by addition of 250 ml of water and removal of 300 ml of solvent was by distillation under reduced pressure at 50° C. The last procedure was repeated twice and finally 250 ml of water was added and 400 ml of solvent was distilled of. The resulting mixture was cooled to 0-5° C. in about one hour. The solid was filtered off and, washed three times with 125 ml of cold water, and dried at 50° C. and 100 mbar under a gentle nitrogen stream till dry. Yield about 94%.

Example 1f

Preparation of 3-[[bis(2-hydroxyethyl)amino]methyl]-1,1'-biphenyl

A mixture was prepared of 123.4 g of diethanolamine, 100 ml of water and 100 ml of methylethylketone (MEK) and 500 ml of methyl t-butyl ether while stirring under a mild nitrogen purge 124.75 g of 3-(bromomethyl)-1,1'-biphenyl was added together with 750 ml of methyl t-butyl ether. The mixture was heated to reflux and refluxed for 18 hours, followed by cooling till room temperature. Thereafter the mixture was washed once with 375 ml of 2N NaOH and four times with 375 ml of water. The combined 2N NaOH and water layers were extracted with 750 ml of methyl t-butyl ether. The combined methyl t-butyl ether layers were washed with 250 ml of water followed by distillation of as much methyl t-butyl ether as possible from the organic layer. 1350 ml of methylethylketone was added and 600 ml of solvent was distilled of at atmospheric pressure. The solution was cooled to room temperature and stored for use in the next step. Yield based on quantitative assay 97%.

Example 1g

Preparation of Bifeprunox Mesylate (Crude)

A solution of 128.9 g of 3-[[bis(2-hydroxyethyl)amino]methyl]-1,1'-biphenyl in approximately 750 ml of methylethylketone prepared according to Example 1f was stirred under mild nitrogen purge. In a separate vessel 202 g of methanesulfonic anhydride was dissolved in 600 ml of methylethylketone at 10-20° C. To the solution of 3-[[bis(2-hydroxyethyl)amino]methyl]-1,1'-biphenyl in methylethylketone 212.8 g of triethylamine was added and 60 ml of methylethylketone. The solution of methanesulfonic anhydride was added in about 45-60 minutes to the 3-[[bis(2-hydroxyethyl)amino]methyl]-1,1'-biphenyl/triethylamine solution, while maintaining the temperature below 10° C. 60 ml of methylethylketone was added and the mixture was stirred for another 15 minutes, followed by drop wise addition of 109.7 g of methanesulfonic acid and addition of 60 ml of methylethylketone in order to rinse the addition vessel.

71.3 g of 7-amino-2(3H)-benzoxazolone, prepared according to Example 1e was suspended in 100 ml of methylethylketone and added to the reaction mixture followed by 60 ml of methylethylketone. The reaction mixture was heated to reflux and refluxed during 20-24 hours. After 20-24 hours of reflux 48 ml of water was added and the mixture was refluxed again for 1 hour. 420 ml of methylethylketone was added and 490 ml of methylethylketone/water was distilled of. This last step was repeated three times. 46.1 g of methanesulphonic acid was added, the mixture was refluxed for an additional hour and cooled down to room temperature in 1 hour. The mixture was further cooled down to 0-5° C. and stirred at this temperature for another hour. The solid was filtered off and, washed twice with 75 ml of cold methylethylketone, and dried at 50° C. and 100 mbar under a gentle nitrogen stream till dry. Yield about 76%.

EXAMPLE 2

Preparation of Polymorphic Form α of Bifeprunox Mesylate in 2-propanol 10.06 g of bifeprunox mesylate crude prepared as described Example 1g was suspended in a mixture of 200 ml of 2-propanol and 40 ml of water under nitrogen purge. The suspension was heated until reflux and cooled down to room temperature in 120 minutes under stirring. The formed suspension was further cooled down under stirring to 0° C. and stirred at this temperature for a further 120 minutes. The crystals were filtered of and dried at 50° C. and 100 mbar.

EXAMPLE 3

Preparation of Polymorphic Form α of Bifeprunox Mesylate in Acetronitrile 50 g of bifeprunox mesylate prepared crude as described in Example 1g was suspended in a mixture of 875 ml of acetonitrile and 250 ml of water under nitrogen purge. 375 ml of acetonitrile was added and the reaction mixture was heated till reflux. 500 ml of solvent was distilled off and 500 ml of acetonitrile were added and this procedure was repeated for a second time. After distilling another 500 ml of solvent the mixture was cooled down to room temperature in 120 minutes. The mixture was further cooled down to 5-0° C. and stirred for 120 minutes at this temperature. The formed crystals were filtered off and washed twice with acetonitrile. The isolated crystals were dried at 50° C. and 100 mbar under a mild nitrogen purge. Yield 85.6%.

EXAMPLE 4

Preparation of Polymorphic Form γ of Bifeprunox Mesylate

To a suspension of 12.50 g of bifeprunox mesylate (crude) prepared as described in Example 1g in 150 ml of methylethylketone (MEK) 75 ml of a 5% $NaHCO_3$ solution was added in about 10-15 min. After 5-10 minutes of stirring the suspension was filtered over Hyflo® or Celite® into another vessel where the layers were separated. The water layer was extracted with 125 and 75 ml of methylethylketone. The methylethylketone layers were combined and washed with a mixture of 50 ml of water and 10 ml of ethanol 96%.

The methylethylketone layer was filtered through a 1 µm filter into a clean vessel, after which the filter was rinsed with 25 ml of methylethylketone. Methylethylketone was distilled off until a volume of about 130 ml was reached, 200 ml of methylethylketone was added and again methylethylketone was distilled off to reach a volume of 175 ml.

Then a solution of 3.00 grams of methane sulphonic acid in 50 ml of methylethylketone was added in about 30 min. After cooling to 5° C. and stirring for 1½ hours at this temperature the product was filtered off and washed twice with 50 ml of cold methylethylketone. After drying at 50° C. and 100 mbar under a mild nitrogen purge the gamma polymorph of bifeprunox mesylate was yielded in about 80%.

EXAMPLE 5

Preparation of a 10 mg Capsule Formulation of Polymorphic Form α of Bifeprunox Mesylate 2.227 kg of lactose was sieved and filled into a high shear mixer. 125 g of bifeprunox mesylate in its polymorphic form α was sieved and added. The composition was mixed with a high shear mixer (e.g. Collette Gral 10 or Collette Gal 75) until it was homogenous (approximately 4 minutes). 24 g of a disintegrant (e.g. sodium starch glycolate USP-NF such as Primojel®) and 24 g of a lubricant (e.g. sodium stearyl fumarate such as PRUV®) were added and the composition was mixed again until it was homogenous (approximately 1 minute). The powder was filled into capsules size 0, 240 mg per capsule by means of a capsule filling machine (e.g. Zanasi LZ 64 or Zanasi RM63 plug filler). Approximately 10,000 filled capsules were obtained.

EXAMPLE 6

Preparation of a 10 mg Tablet Formulation of Bifeprunox Mesylate Polymorphic Form α

Tablets with a strength of 10 mg were prepared according to the following procedures (required quantities are given in Table 8). One third of the given amount of lactose monohydrate was sieved and filled into a high shear mixer and mixed during 5 minutes. The required amount of milled bifeprunox mesylate in its polymorphic form α was added to the mixture, together with 0.100 kg sodium starch glycolate, type A, 2.32 kg microcrystalline cellulose and the remainder of the lactose monohydrate. The composition was mixed with a high shear mixer (e.g. Collette Gral 10 or Collette Gal 75) until it was homogenous (approximately 10 minutes). The required amount of a sodium stearyl fumarate (such as PRUV®), sieved through a 0.42 mm sieve was added and the composition was mixed again until it was homogenous (approximately 5 minutes). The final product was compressed with 300 MPa into tablets. The product was coated using 15% in/in of the indicated Opadry II HP water suspension to 3.5% of the core weight.

Table 8 shows the amount of active ingredient and auxiliary materials used in a large scale production of 10 mg bifeprunox mesylate tablets.

TABLE 8 shows the amount of active ingredient and auxiliary materials used in a large scale production of 10 mg bifeprunox mesylate tablets.

| Components | Per batch of 83333 10 mg tablets (in kg) |
|---|---|
| Core components | |
| Bifeprunox mesylate (milled) | 1.041 |
| Lactose monohydrate | 16.33 |
| Microcrystalline cellulose | 2.32 |
| Sodium starch glycolate, type A | 0.100 |
| Sodium stearyl fumarate | 0.200 |
| Coating components | |
| Opadry II HP beige 85F27126 | 0.700 |
| Purified water | 3.968 |

EXAMPLE 7

Analytical Methods

XRPD patterns were measured on a diffractometer using monochromatic CuKα radiation (tube voltage 40 kV, tube current 40 mA) at room temperature. IR spectra were recorded on a Fourier transform IR spectrometer in attenuated total reflectance (silicon crystal) with a spectral resolution of 2 $cm^{-1}$ using a mercury cadmium telluride detector.

Melting points were determined on a DSC apparatus as onset temperatures of the melting endotherm using 40 µL aluminum crucibles with a pierced lid. Temperature program: heating from 25° C. up to 300° C. with 10 K $min^{-1}$. $N_2$ atmosphere at a flow of 80 mL $min^{-1}$.

The solid state $^{13}C$ NMR spectra were obtained using the cross-polarisation magic-angle spinning (CP/MAS) accessory on a Bruker AM300 instrument (contact time of 4 ms, recycle delay 3 s, spectral width 30 kHz, $^1H$ 90° pulse of 6 µs, spinning rate about 8.5 kHz. A standard 4 mm Bruker CP/MAS probe was used. Chemical shifts are referred to glycine ($\delta_c$=176.03 ppm for the C=O resonance).

Analyses for the alpha and the delta crystal forms were carried out at the Bijvoet Centre for Biomolecular Research, Utrecht University. Analysis of the gamma crystal form was carried out in Peter Jones' lab in Institute of Inorganic and Analytical Chemistry, University of Braunsweig.

Crystals of the alpha form appeared under the microscope as block-shaped, those of the gamma crystal form were plate- or rod-shaped, whereas crystals of the delta crystal form looked block-shaped with rounded edges.

For each crystal form, a crystal was transferred into the cold nitrogen stream on a rotating anode X-ray diffractometer. The structures were solved by automated direct methods. Hydrogen atoms bonded to nitrogen were located on an electron-density map and their coordinates were included as parameters in the refinement. Other hydrogen atoms were included in the refinement on calculated positions riding on their carrier atoms. All non-hydrogen atoms were refined with anisotropic atomic displacement parameters. Hydrogen atoms were given fixed displacement factors, related to those of their carrier atoms.

The invention claimed is:

1. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits an X-ray powder diffraction pattern having characteristic peaks expressed in degrees 2θ at approximately 7.0, 9.3, 10.0, 12.5, 15.4, 16.7, 17.2, 17.4, 17.7, 18.7, 21.3, 22.2, 25.2, 27.2, 28.3, 28.8 and 30.1.

2. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph has a melting point of about 277° C.

3. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a DSC trace as shown in FIG. 2.

4. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits an attenuated total reflectance infrared spectrum having characteristic absorption bands expressed in reciprocal centimeters at approximately 1764, 1217, 795, 746 and 694.

5. The pharmaceutical composition according to claim 4, wherein the crystalline polymorph exhibits an attenuated total reflectance infrared spectrum having characteristic absorption bands expressed in reciprocal centimeters at approximately 1764, 1636, 1284, 1217, 809, 795, 746, 694, 663 and 509.

6. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient
wherein the crystalline polymorph exhibits an IR spectrum as shown in FIG. 3.

7. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits $^{13}$C solid state NMR chemical shifts expressed relative to glycine ($\delta_c$=176.03 for the C=O resonance) at approximately 40.4, 48.7, 56.5, 106.8 and 137.7 ppm.

8. The pharmaceutical composition according to claim 7, wherein the crystalline polymorph exhibits $^{13}$C solid state NMR chemical shifts expressed relative to glycine ($\delta_c$=176.03 for the C=O resonance) at approximately 40.4, 48.7, 50.3, 56.5, 106.8, 110.7, 124.9, 126.9, 127.8, 129.2, 130.8, 134.2, 137.7, 141.6, and 153.8 ppm.

9. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a complete $^{13}$C solid state NMR chemical as shown in FIG. 4.

10. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a single crystal X-ray crystallographic analysis at 150K with (a) crystal parameters that are approximately equal to the following:

| Cell dimensions | a = 9.283 Å |   |
|---|---|---|
|   | b = 10.737 Å |   |
|   | c = 12.690 Å |   |
|   | α = 98.553° |   |
|   | β = 93.749° |   |
|   | γ = 116.097° |   |
|   | Crystal system triclinic |   |
|   | Space group | P-1 |
|   | Molecules/unit cell | 2 |
|   | Density (g/cm$^3$) 1.481 |   | and (b) atomic positions of all atoms relative to the origin of the unit cell as recited in Table 5.

11. A pharmaceutical composition comprising an effective amount of a crystalline polymorph of 7-[4-([1,1'-biphenyl]-3-ylmethyl)-1-piperazinyl]-2(3H)-benzoxazolone monomethanesulfonate and at least one pharmaceutically acceptable excipient,
wherein the crystalline polymorph exhibits a single X-ray diffraction substantially as shown in FIG. 5.

12. A pharmaceutical composition comprising an effective amount of 7-[4-([1,1'-biphenyl]-3-ylmethyl)-1-piperazinyl]-2(3H)-benzoxazolone monomethanesulfonate wherein the effective amount of 7-[4-([1,1'-biphenyl]-3-ylmethyl)-1-piperazinyl]-2(3H)-benzoxazolone monomethanesulfonate is a mixture of the crystalline polymorphic forms α and γ, and at least one pharmaceutically acceptable excipient.

13. A pharmaceutical composition comprising an effective amount of 7-[4-([1,1'-biphenyl]-3-ylmethyl)-1-piperazinyl]-2(3H)-benzoxazolone monomethanesulfonate in which at least about 50 weight % of the 7-[4-([1,1'-biphenyl]-3-ylmethyl)-1-piperazinyl]-2(3H)-benzoxazolone monomethanesulfonate is in the crystalline polymorphic form α, and at least one pharmaceutically acceptable excipient.

14. The composition according to claim 13, wherein at least about 60 weight % of the 7-[4-([1,1'-biphenyl]-3-ylmethyl)-1-piperazinyl]-2(3H)-benzoxazolone monomethanesulfonate is in the crystalline polymorphic form α.

15. The composition according to claim 14, wherein at least about 80 weight % of the 7-[4-([1,1'-biphenyl]-3-ylmethyl)-1-piperazinyl]-2(3H)-benzoxazolone monomethanesulfonate is in the crystalline polymorphic form α.

16. The composition according to claim 15, wherein at least about 90 weight % of the 7-[1,1'-biphenyl]-3-ylmethyl)-1-piperazinyl]-2(3H)-benzoxazolone monomethanesulfonate is in the crystalline polymorphic form α.

17. The composition according to claim 16, wherein at least about 95 weight % of the 7-[4-([1,1'-biphenyl]-3-ylmethyl)-1-piperazinyl]-2(3H)-benzoxazolone monomethanesulfonate is in the crystalline polymorphic form α.

18. A pharmaceutical composition comprising an effective amount of 7-[4-([1,1'-biphenyl]-3-ylmethyl)-1-piperazinyl]-2(3H)-benzoxazolone monomethanesulfonate and at least one auxiliary material chosen from lactose monohydrate, microcrystalline cellulose, sodium starch glycolate type A and sodium stearyl fumarate.

19. The pharmaceutical composition according to claim 18, wherein:
   said effective amount of 7-[4-([1,1'-biphenyl]-3-ylmethyl)-1-piperazinyl]-2(3H)-benzoxazolone monomethanesulfonate comprises an effective amount of crystalline polymorphic form α;
   said lactose monohydrate is present in an amount ranging from about 70% to about 90% w/w;
   said microcrystalline cellulose is present in an amount ranging from about 10% to about 15% w/w;
   said sodium starch glycolate type A is present in an amount ranging from about 0.3% to about 0.7% w/w;
   said sodium stearyl fumarate is present in an amount ranging from about 0.6% to about 1.3% w/w;
   and optionally comprising colloidal anhydrous silica present in an amount ranging from 0 to about 0.5% w/w.

20. The pharmaceutical composition according to claim 18, wherein said effective amount of 7-[4-([1,1'-biphenyl]-3-ylmethyl)-1-piperazinyl]-2(3H)-benzoxazolone monomethanesulfonate comprises an effective amount of a mixture of the crystalline polymorphic forms α and γ.

21. The pharmaceutical composition according to claim 20, wherein:
   said effective amount of 7-[4-([1,1'-biphenyl]-3-ylmethyl)-1-piperazinyl]-2(3H)-benzoxazolone monomethanesulfonate comprises an effective amount of the crystalline polymorphic forms α and γ;
   said lactose monohydrate is present in an amount ranging from about 70% to about 90% w/w;
   said microcrystalline cellulose is present in an amount ranging from about 10% to about 15% w/w;
   said sodium starch glycolate type A is present in an amount ranging from about 0.3% to about 0.7% w/w;
   said sodium stearyl fumarate is present in an amount ranging from about 0.6% to about 1.3% w/w;
   and optionally comprising colloidal anhydrous silica present in an amount ranging from 0 to about 0.5% w/w.

22. A method for treating a CNS disorder in a human patient in need thereof, comprising administering to the patient a pharmaceutical composition comprising the crystalline polymorphic form α of 7 [4-([1,1'-biphenyl]-3-ylmethyl)-1-piperazinyl]-2(3H)-benzoxazolone monomethanesulfonate in an amount effective for treatment of the disorder, wherein said CNS disorder is schizophrenia.

23. A method for treating a CNS disorder in a human patient in need thereof, comprising administering to the patient a pharmaceutical composition comprising the crystalline polymorphic form α of 7-[4-([1,1'-biphenyl]-3-ylmethyl)-1-piperazinyl]-2(3H)-benzoxazolone monomethanesulfonate in an amount effective for treatment of the disorder, wherein said CNS disorder is chosen from a psychotic disorder and Parkinson's disease.

24. A method for treating a CNS disorder in a human patient in need thereof, comprising administering to the patient a pharmaceutical composition comprising a mixture of the polymorphic forms α and γ of 7-[4-([1,1'-biphenyl]3-ylmethyl)-1-piperazinyl]-2(3H)-benzoxazolone monomethanesulfonate in an amount effective for treatment of the disorder, wherein said CNS disorder is schizophrenia.

25. A method for treating a CNS disorder in a human patient in need thereof, comprising administering to the patient a pharmaceutical composition comprising a mixture of the polymorphic forms α and γ of 7-[4-([1,1'-biphenyl]3-ylmethyl)-1-piperazinyl]-2(3H)-benzoxazolone monomethanesulfonate in an amount effective for treatment of the disorder, wherein said CNS disorder is chosen from a psychotic disorder and Parkinson's disease.

* * * * *